United States Patent
Nilsson et al.

(10) Patent No.: US 11,894,106 B2
(45) Date of Patent: Feb. 6, 2024

(54) SYSTEMS AND METHODS FOR DATA COMMUNICATION, STORAGE, AND ANALYSIS USING REFERENCE MOTIFS

(71) Applicant: Intertrust Technologies Corporation, Milpitas, CA (US)

(72) Inventors: Jarl A. Nilsson, Mountain View, CA (US); William Knox Carey, Mountain View, CA (US)

(73) Assignee: Intertrust Technologies Corporation, Berkeley, CA (US)

( * ) Notice: Subject to any disclaimer, the term of this patent is extended or adjusted under 35 U.S.C. 154(b) by 1083 days.

(21) Appl. No.: 16/057,357

(22) Filed: Aug. 7, 2018

(65) Prior Publication Data
US 2019/0042694 A1 Feb. 7, 2019

Related U.S. Application Data

(60) Provisional application No. 62/542,203, filed on Aug. 7, 2017.

(51) Int. Cl.
*G16B 30/00* (2019.01)
*G16B 20/20* (2019.01)
*G16B 30/10* (2019.01)
*G16B 30/20* (2019.01)

(52) U.S. Cl.
CPC .............. *G16B 30/10* (2019.02); *G16B 20/20* (2019.02); *G16B 30/00* (2019.02); *G16B 30/20* (2019.02)

(58) Field of Classification Search
CPC .................. G16B 20/20; G16B 30/00
See application file for complete search history.

(56) References Cited

U.S. PATENT DOCUMENTS

| 2013/0031092 A1* | 1/2013 | Bhola | H03M 7/46 |
| | | | 707/E17.089 |
| 2018/0121601 A1* | 5/2018 | Hahm | G16B 50/40 |

OTHER PUBLICATIONS

Huang, J., Liang, X., Xuan, Y., Geng, C., Li, Y., Lu, H., Qu, S., Mei, X., Chen, H., Yu, T. and Sun, N., 2017. A reference human genome dataset of the BGISEQ-500 sequencer. GigaScience, 6(5), p.gix024. (Year: 2017).*
Nguyen, VH. and Lavenier, D., 2009. PLAST: parallel local alignment search tool for database comparison. BMC Bioinformatics, 10(1), pp. 1-13. (Year: 2009).*
Rizk, G. and Lavenier, D. Gassst: global alignment short sequence search tool. Bioinformatics, 26(20), pp. 2534-2540. (Year: 2010).*

* cited by examiner

*Primary Examiner* — Lori A. Clow
*Assistant Examiner* — Janna Nicole Schultzhaus
(74) *Attorney, Agent, or Firm* — Finnegan, Henderson, Farabow, Garrett & Dunner, LLP

(57) ABSTRACT

Systems and methods for communicating, storing, and/or analyzing data that may include genomic data are described herein. In various embodiments, unaligned genomic sequence read data and/or portions thereof may be stored and/or communicated as a list of variants relative to a particular reference associated with a reference motif identified in the genomic sequence read data. In further embodiments, quality score information associated with a genomic dataset may be analyzed and/or communicated as quality score parameter information. Additional embodiments may facilitate relatively efficient analysis of unaligned genomic sequence read data using metadata associated with reference motifs identified in the unaligned genomic sequence read data.

10 Claims, 8 Drawing Sheets

SYSTEMS AND METHODS FOR DATA COMMUNICATION, STORAGE, AND ANALYSIS USING REFERENCE MOTIFS

RELATED AUTHORIZATION

This application claims the benefit of priority under 35 U.S.C. § 119(e) to U.S. Provisional Patent Application No. 62/542,203, filed Aug. 7, 2017, and entitled "SYSTEMS AND METHODS FOR DATA COMMUNICATION AND STORAGE USING REFERENCE MOTIFS," the contents of which is hereby incorporated by reference in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

SUMMARY

The present disclosure relates generally to the communication, storage, and analysis of data. More specifically, but not exclusively, the present disclosure relates to systems and methods for efficient communication, storage, and analysis of genomic data using reference motifs.

Genetic testing is moving from detection of Single Nucleotide Polymorphisms ("SNPs")—isolated individual chemical differences in genetic code—to Whole Genomic Sequencing ("WGS"), which records every base pair in a genetic sequencing. Genomic sequencing information may be utilized in connection with a variety of applications including, for example, molecular and evolutionary biology studies. For example, in molecular biology studies, genomic information may be utilized in connection with identifying new genes, identifying potential drug targets, identifying genetic associations with certain diseases and/or conditions, and/or the like.

Genomic data, including the genomes of human beings, tumors, and/or viruses can be very large (e.g., 3 billion base pairs). Three billion base pairs may be electronically encoded in approximately 700 megabytes of data. Given this relatively large size, communicating and/or storing a large number of genomic datasets may require significant communication and/or storage capacity. Similarly, analysis of large number of genomic datasets may involve a significant amount of computational resources.

Sequence information generated by a genetic material sequencing system may, in certain instances, comprise unaligned sequence read data associated with a plurality of sequenced partial DNA strands. A complete sequence may be reconstructed from the unaligned sequence read data by aligning the data. This alignment process may, however, be relatively computationally intensive. Accordingly, it may be desirable to communicate unaligned sequence read data to a system with greater computational resources to perform the alignment process.

Embodiments of the systems and methods disclosed herein may facilitate relatively efficient communication and/or storage of data including, for example, genomic data such as unaligned sequence read data. In certain embodiments, certain sequence patterns, which may be referred to herein as "motifs" and/or "reference motifs" may be identified in unaligned sequence read data. Each motif may be associated with one or more known reference sequences. In certain embodiments, reference motifs may comprise relatively unique sequence patterns that have a relatively strong association with a corresponding reference sequence. That is, the presence of a reference motif sequence pattern in sequence read data may be associated with a likelihood that the sequence also includes the reference sequence associated with the reference motif.

Once a motif has been identified in the unaligned sequence read data, the reference sequence and/or portions thereof associated with the motif may be compared with the unaligned sequence read data and/or portions thereof to determine a difference between the datasets, which may be referred to herein as variants. In some embodiments, the unaligned sequence read data and/or portions thereof may be stored and/or communicated as a list of variants relative to a particular reference associated with the identified motifs, thereby realizing certain efficiencies.

Further embodiments of the disclosed systems and methods may facilitate relatively efficient communication and/or storage of quality scores associated with sequence read data. In certain embodiments, sequence read data may be associated with one or more quality scores that may represent a relative confidence in a particular read of a location in a particular sequence strand. Quality scores associated with a sequence strand may be represented by a quality score curve. Consistent with embodiments disclosed herein, a quality score curve may be analyzed to determine one or more parameters that describe the quality score curve (e.g., analyzed via polynomial and/or other curve fitting methods, by comparing a quality score curve with one or more reference curves, and/or the like). In certain embodiments, the one or more parameters associated with the analyzed quality score curve may be communicated and/or stored in place of discrete quality score data and/or the entire associated quality curve, thereby realizing certain efficiencies.

Additional embodiments of the disclosed systems and methods may facilitate relatively efficient analysis of sequence read data. In certain embodiments, one or more reference motifs comprising certain sequence patterns may be identified in unaligned sequence read data. The reference motifs may be associated with certain metadata and/or other information. The metadata and/or other information may, among other things, delineate information relating to characteristics, traits, and/or classifications of an organism associated with sequence read data that includes a particular reference motif. By identifying a reference motif within unaligned sequence read data, the unaligned sequence read data may be associated with the corresponding metadata and/or other information associated with the identified reference motif.

BRIEF DESCRIPTION OF THE DRAWINGS

The inventive body of work will be readily understood by referring to the following detailed description in conjunction with the accompanying drawings, in which.

DETAILED DESCRIPTION

Figure 1B:
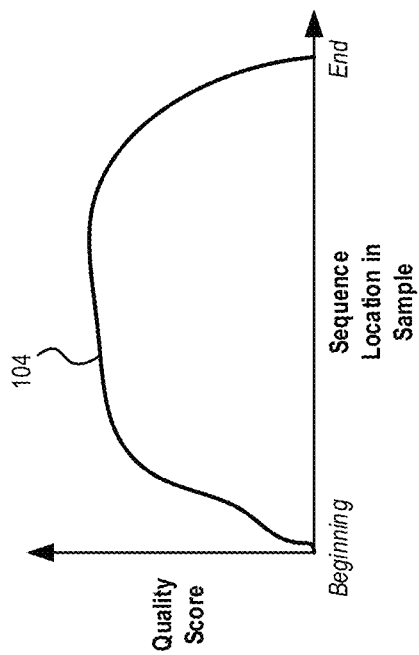
FIG. 1B illustrates an example of quality score distribution based on sequence location on a sequenced strand consistent with embodiments of the present disclosure.

A detailed description of the systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of any method disclosed herein do not necessarily need to be executed in any specific order, or even sequentially, nor need the steps be executed only once, unless otherwise specified.

Systems and methods are presented that may facilitate efficient communication, storage, and/or analysis of genomic and/or bioinformatic information that includes unaligned sequence read data. As used herein, the terms "datasets," "genomic data," "genomic information," "genome," and/or "genomic datasets," sequence data," "unaligned sequence read data," and/or variations thereof may generally refer to data expressing, representing, and/or derived from the entirety or a portion of a genome or genome sequence and, in certain instances herein, may be used interchangeably. This data may include, without limitation, information encoded in chemical structures such as DNA, mRNA, and proteins as well as related regulatory information such as methylation status. As used herein, the term "genome" may refer to an organism's hereditary information. A genome may be encoded in DNA or RNA, and may be represented as mRNA or as protein sequences derived from these nucleic acid sequences. The term "genome" may include both genes and non-coding sequences. When applied to a specific organism, the term "genome" can refer to genomic data from normal cells—including mitochondrial DNA—and also genomic data from related cells such as tumors and other organisms of the microbiome. Although embodiments of the disclosed systems and methods are discussed herein in connection with unaligned sequence read data, it will be appreciated that the disclosed systems and methods may also be used in connection with any other suitable information and/or data including any other type of bioinformatic information.

Sequence read data including, for example, unaligned sequence read data may be output as a result of a variety of genetic sequence processes and may be generated by any suitable system for identifying and/or otherwise generating a genetic sequence associated with a genetic material—that is, any suitable system for determining the order of nucleotides within a DNA molecular of a genetic material. Such a system may employ a variety of gene sequencing technologies including, for example, one or more of Maxam-Gilbert sequencing, chain-termination sequencing, shotgun sequencing, bridge PCR sequencing, single-molecular real-time sequencing, ion semiconductor sequencing, pyrosequencing, sequencing by synthesis, sequencing by ligation, nanopore sequencing, chain termination sequencing, massively parallel signature sequencing, polony sequencing, parallelized pyrosequencing, dye sequencing, DNA nanoball sequencing, heliscope single molecule sequencing, single-molecule real-time sequencing, and/or any other type of genetic sequencing technology and/or process.

Figure 1A:
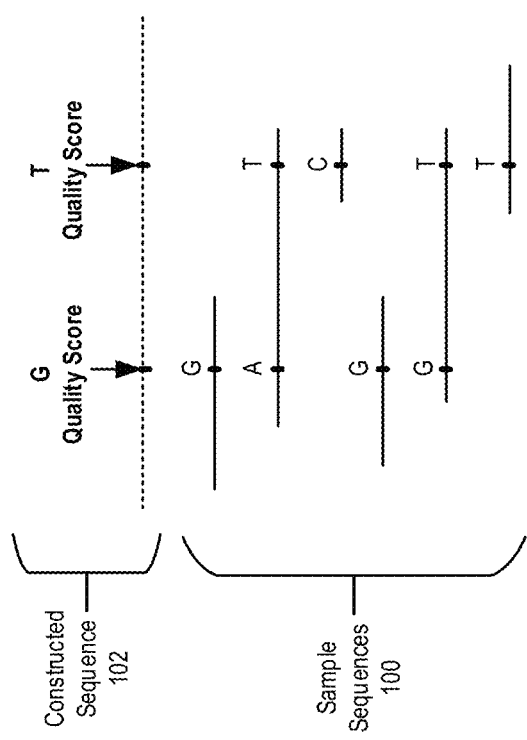
FIG. 1A illustrates an example of unaligned sequence read data and a constructed sequence consistent with embodiments of the present disclosure.

FIG. 1A illustrates an example of unaligned sequence read data 100 and a constructed sequence 102 consistent with embodiments of the present disclosure. As illustrated in FIG. 1A, sequence information generated by a genetic material sequencing system may comprise unaligned sequence read data 100, which may in certain instances herein also be referred to herein as sample sequence data. The unaligned sequence read data 100 may be associated with a plurality of sequenced partial strands of genetic material.

A complete and/or partially complete constructed sequence 102 may be reconstructed from the unaligned sequence read data 100 through an alignment process. Unaligned sequence read data 100 associated individual sequenced partial strands may be aligned in a manner such that read data associated with the positions of various strands in an associated complete sequence is aligned or is relatively aligned and/or in agreement. Based on the aligned sequenced strands, a complete sequence 102 may be constructed.

In certain embodiments, read data from a sequencer associated with certain sequenced partial strands may not align perfectly with read data associated with other partial strands. For example, as illustrated, sequence read data 100 of a relatively large number of strands may indicate guanine ("G") in a particular sequence position, but a certain subset of strands may indicate adenine ("A"). In certain embodiments, it may be determined that the sequence location is likely a G based on the relative degree of alignment and/or agreement. For example, if a majority and/or a threshold number of aligned partial stands indicate a particular nucleobase at a sequence location, then the indicated nucleobase is likely to be the actual nucleobase at the sequence location.

A quality score, such as a Phred quality score, may be associated with the particular sequence location that reflects a likelihood that the sequence location is a particular nucleobase. That is, the quality score may measure a quality and/or relative likelihood that the identification of the nucleobases generated by the sequencing system is accurate. In this manner, quality scores may represent a relative confidence in a particular read of a partial sequence location in a genomic sequence.

Quality scores may also be influenced based, at least in part, on a position of a sequence location relative to an associated sequenced strand. FIG. 1B illustrates an example of a quality score distribution 104 based on sequence location on a sequenced strand consistent with embodiments of the present disclosure. For example, as illustrated, quality scores may be generally lower for sequence locations at the ends of a sequence strand of DNA than in the middle of a sequence strand (e.g., due to handling of the partial strand ends during the sequencing process and/or the like).

Figure 2:
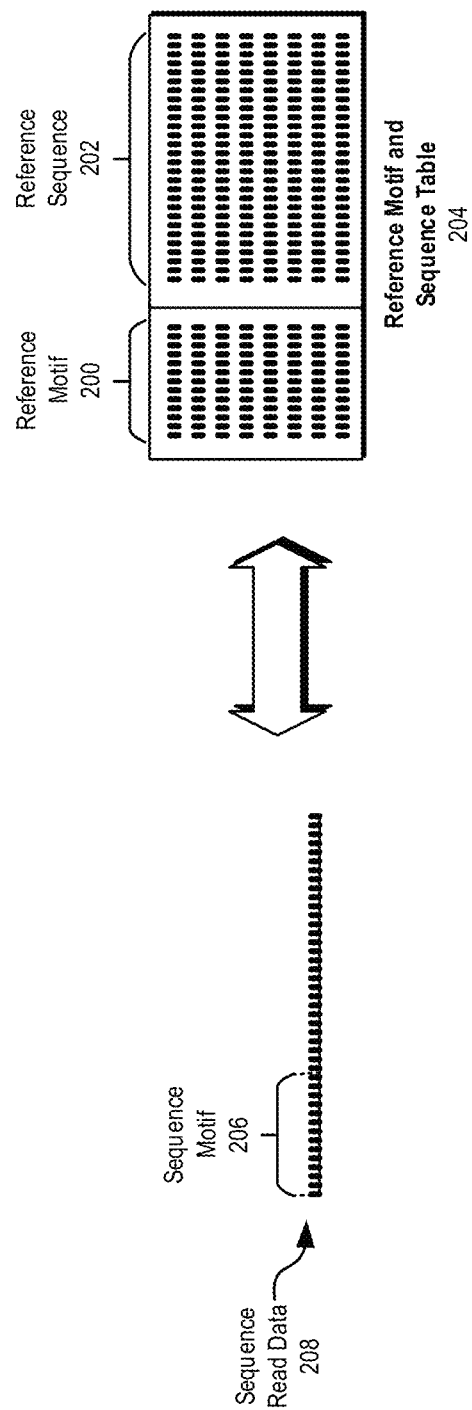
FIG. 2 illustrates an example of the use of reference motifs in connection with the storage and/or communication of unaligned sequence read data consistent with embodiments of the present disclosure.

FIG. 2 illustrates an example of the use of reference motifs 200 in connection with the storage and/or communication of unaligned sequence read data 208 consistent with embodiments of the present disclosure. A reference motif 200 may be associated with a reference sequence 202 that either includes and/or follows the motif. Reference motifs 200 consistent with various disclosed embodiments may comprise sequence patterns of a variety of suitable lengths (e.g., 8 base pairs, 16 base pairs, etc.).

As an example, in a reference sequence that is 80 positions long, the first 16 positions may comprise the reference motif 200, and the following 64 positions may comprise the reference sequence information 202 associated with the motif 200. A plurality of reference motifs 200 and associated reference sequence information 202 may be stored in a table 204 and/or any other suitable format. In some embodiments, a reference motif 200 may function similarly to a header and/or a prefix, providing an index location in the reference motif and sequence table 204 associated with a particular reference sequence information 202.

In certain embodiments, reference motifs 200 may be identified prebuilt by analyzing a large number of unaligned sequence data samples and identifying relatively unique sequence patterns that have a relatively strong association with a corresponding sequence (e.g., using pattern analysis techniques and/or the like). That is, sequence patterns that, when present in unaligned sequence data, may be associated with a relatively high likelihood that the sequence data also includes other sequence data (e.g., reference sequence data) may be identified as reference motifs 200. In further embodiments, libraries and/or tables of reference motifs 200 may be dynamically built. For example, as a reference dataset grows as sequence data is ingested, patterns and/or associated may become more readily identifiable and used as reference motifs. In this manner, reference motifs 200 may be identified as part of a dynamic data learning process.

Consistent with various disclosed embodiments, a sequence read data 208 may be analyzed to determine whether the data includes a reference motif 200. If a reference motif 200 included in the reference motif and associated sequence table 204 is identified in the sequence read data 208 (e.g., identified as a sequence motif 206), the reference sequence information 202 and/or portions thereof associated with the reference motif 200 may be compared with the unaligned sequence read data associated with the sequence read data 208 and/or portions thereof to determine a difference between the datasets 202, 208. Any differences between the datasets 202, 208 may be included in a variant list associated with the sequence read data 208. In some embodiments, the sequence read data 208 and/or portions thereof may be stored and/or communicated as such a variant list with reference to a particular reference motif 200 and/or reference sequence 202, thereby realizing certain storage and/or communication efficiencies. The sequence read data 208 may be reconstructed using the variant list and the reference sequence information 202 associated with the motif 200.

Figure 3:
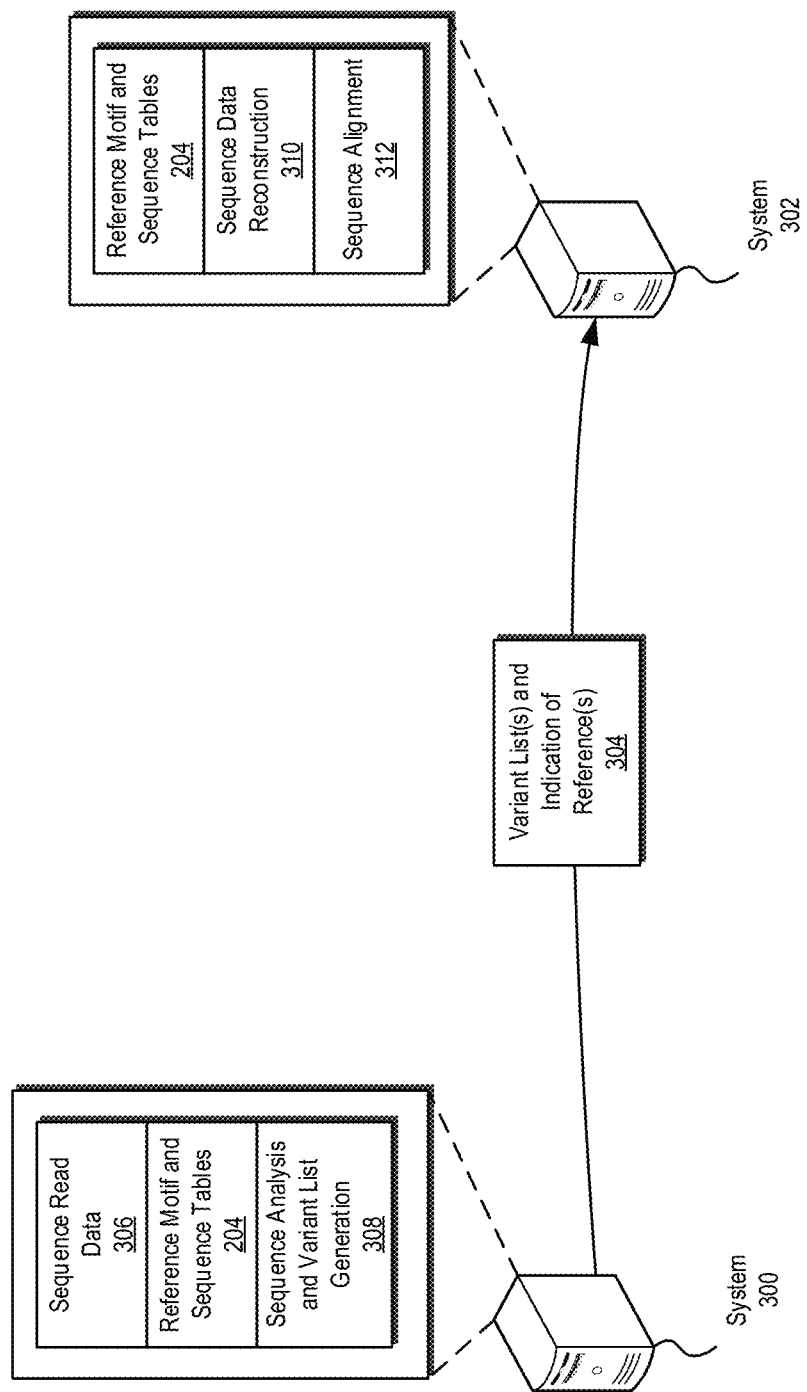
FIG. 3 illustrates an example of the communication of unaligned sequence read data between systems consistent with embodiments of the present disclosure.

FIG. 3 illustrates an example of the communication of unaligned sequence read data (e.g., sample sequences 306) between systems 300, 302 consistent with embodiments of the present disclosure. Consistent with various embodiments disclosed herein, unaligned sequence read data may be communicated between systems 300, 302 as variant lists and indications of reference data 304 associated with the variant lists.

The systems 300, 302 may comprise a variety of computing devices and/or systems, including any computing system or systems suitable to implement the systems and methods disclosed herein. The systems 300, 302 may comprise a variety of computing devices and systems, including laptop computer systems, desktop computer systems, server computer systems, distributed computer systems, smartphones, tablets, and/or the like. It will be appreciated that any suitable configuration of computing systems and storage media could be used in connection with the systems 300, 302, including without limitation, a single server or cluster of servers, and/or a distributed collection of heterogeneous computer systems connected by a variety of networks (e.g., such as the Internet, public and/or private networks, and/or the like).

In certain embodiments, the systems 300, 302 may comprise at least one processor system configured to execute instructions stored on an associated non-transitory computer-readable storage medium. As discussed in more detail below, the systems 300, 302 may further comprise a secure processing unit ("SPU") configured to perform sensitive operations such as trusted credential and/or key management, secure policy management, and/or other aspects of the systems and methods disclosed herein. The systems may further comprise software and/or hardware configured to enable electronic communication of information between the devices and/or systems 300, 302 via a network using any suitable communication technology and/or standard.

The systems 300, 302 may be communicatively coupled via a network employing a variety of network communication devices and/or channels and may utilize any suitable communication protocols and/or standards facilitating communication between the systems 300, 302 and/or one or more other systems and/or services. The network may comprise the Internet, a local area network, a virtual private network, and/or any other communication network utilizing one or more electronic communication technologies and/or standards (e.g., Ethernet or the like). In some embodiments, the network may comprise a wireless carrier system, such as a personal communications system ("PCS"), and/or any other suitable communication system incorporating any suitable communication standards and/or protocols. In further embodiments, the network may comprise an analog mobile communications network and/or a digital mobile communications network utilizing, for example, code division multiple access ("CDMA"), Global System for Mobile Communications or Groupe Speciale Mobile ("GSM"), frequency division multiple access ("FDMA"), and/or time divisional multiple access ("TDMA") standards. In certain embodiments, the network may incorporate one or more satellite communication links. In yet further embodiments, the network may utilize IEEE's 802.11 standards, Bluetooth®, ultra-wide band ("UWB"), Zigbee®, and/or any other suitable standard or standards.

A user of a first system 302 may be interested in communicating and/or storing unaligned sequence read data 306 to and/or by a second system 302. For example, the first system 302 may not have sufficient computational resources to efficiently analyze and/or perform an alignment process of the unaligned sequence read data 306. Accordingly, the user of the first system 300 may wish to communicate the unaligned sequence read data 306 to a second system 302 that has greater computational resources, allowing for a more efficient alignment process.

The first system 300 and the second system 302 may store corresponding tables 204 that comprise a plurality of reference motifs and associated reference sequence information. Although various embodiments disclosed herein may describe reference motifs and associated reference sequence information as being stored in a table 204, it will be appreciated that reference motifs and associated reference sequence data may be stored and/or otherwise maintained by the systems 300, 302 in any suitable format.

Consistent with various disclosed embodiments, a sequence analysis and/or variant list generation module 308 executing on the first system 300 may analyze the unaligned sequence read data 306 to determine whether the sequence read data 306 includes one or more reference motifs included in the reference motif and reference sequence table 204. If a reference motif included in the reference motif and reference sequence table 204 is identified in the unaligned sequence read data 306, the unaligned sequence read data 306 and/or a portion thereof may be compared with the reference sequence associated with the identified reference motif in the table 204 to determine difference(s) between the unaligned sequence read data 306 and the reference sequence.

Differences between the unaligned sequence read data 306 and the reference sequence may be reflected in a variant list generated by the sequence analysis and variant list generation module 308. The variant list and an indication of a reference to a particular reference motif and/or reference sequence 304 may be communicated from the first system 300 to the second system 302. A sequence data reconstruction module 310 executing on the second system 302 may reconstruct the sequence read data 306 using the received variant list 304 and the associated reference motif and/or reference sequence included in the reference motif and/or reference sequence table 204. For example, by applying "diffs" and/or null entries reflected in the received variant list 304 to associated reference sequences included in the reference motif and/or reference sequence table 204, the original unaligned sequence read data 306 may be reconstructed. In various embodiments, the second system 302 may engage in an alignment process of any reconstructed unaligned sequence read data using a sequence alignment module 312.

It will be appreciated that a number of variations can be made to the architecture and relationships presented in connection with FIG. 3 within the scope of the inventive body of work. For example, in some embodiments, the reference motif and/or reference sequence table 204 may be stored and/or otherwise managed by a third-party system and/or service, and the first and second systems 300, 302 may communicate with the third-party system and/or service to access the reference motif and/or reference sequence table 204 in connection with aspects of the various disclosed operations. In further embodiments, one or more other services and/or systems not necessarily illustrated may be utilized in connection with implementing various aspects of the embodiments of the disclosed systems and methods. Although certain embodiments are discussed in connection with storing and/or transmitting genomic data, it will be appreciated that the disclosed embodiments may be further used in connection with efficiently storing and/or communicating any suitable type of information. Thus, it will be appreciated that FIG. 3 is provided for purposes of illustration and explanation, and not limitation.

Figure 4:
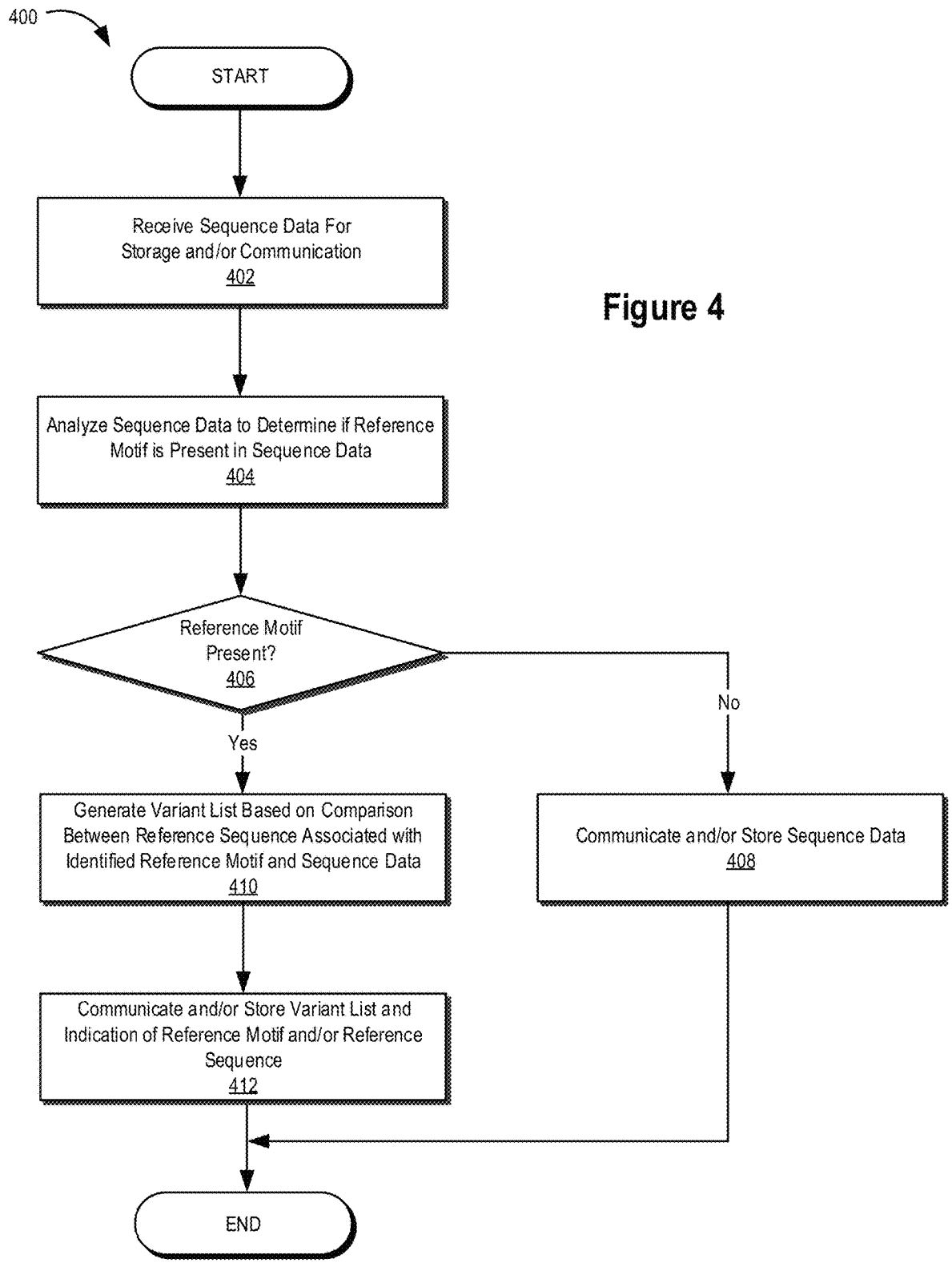
FIG. 4 illustrates a flow chart of an example of a method for storing and/or communicating unaligned sequence read data consistent with embodiments of the present disclosure.

FIG. 4 illustrates a flow chart of an example of a method 400 for storing and/or communicating unaligned sequence read data consistent with embodiments of the present disclosure. The illustrated method 400 may be implemented in a variety of ways, including using software, firmware, hardware, and/or any combination thereof. In certain embodiments, various aspects of the method 400 and/or its constituent steps may be performed by a genomic data storage and/or processing system and/or any other suitable system or combination of systems. In some embodiments, the illustrated method 400 may facilitate the generation and/or communication of unaligned sequence read data using variant lists generated based on identified motifs in the unaligned sequence read data.

At 402, sequence data for storage by and/or communication from a system may be received. In certain embodiments, the sequence data may comprise unaligned sequence read data. For example, the sequence data may comprise unaligned sequence read data associated with a plurality of sequenced partial DNA strands.

The sequence data may be analyzed at 404 to determine if the sequence data includes one or more reference motifs. In some embodiments, the sequence data may be analyzed to determine whether the sequence data includes one or more reference motifs that are included in a reference motif and reference sequence table. If it is determined that the original sequence data does not include a reference motif at 406, the method 400 may proceed to 408, and the sequence data may be stored by and/or communicated from the system. Otherwise, if it is determined at 406 that the sequence data includes at least one reference motif, the method 400 may proceed to 410.

The sequence data and/or portions thereof may be compared with the reference sequence and/or portions thereof associated with the identified reference motif. Based on the comparison, a variant list may be generated at 410 indicative of one or more differences between the sequence data and/or portions thereof and the reference sequence and/or portions thereof. The sequence data may then be stored by and/or communicated from the system at 412 as the generated list of variants relative to a particular indicated reference motif and/or sequence.

The sequence data may be reconstructed using the variant list and the reference motif and/or reference sequence associated with the variant list. For example, the variant list may be associated with a pointer, reference motif, and/or any other suitable indication identifying an entry in a table of one or more reference motifs and/or reference sequences. By applying diffs reflected in the received variant list to the associated reference sequences, the original unaligned sequence read data may be reconstructed.

Figure 5:
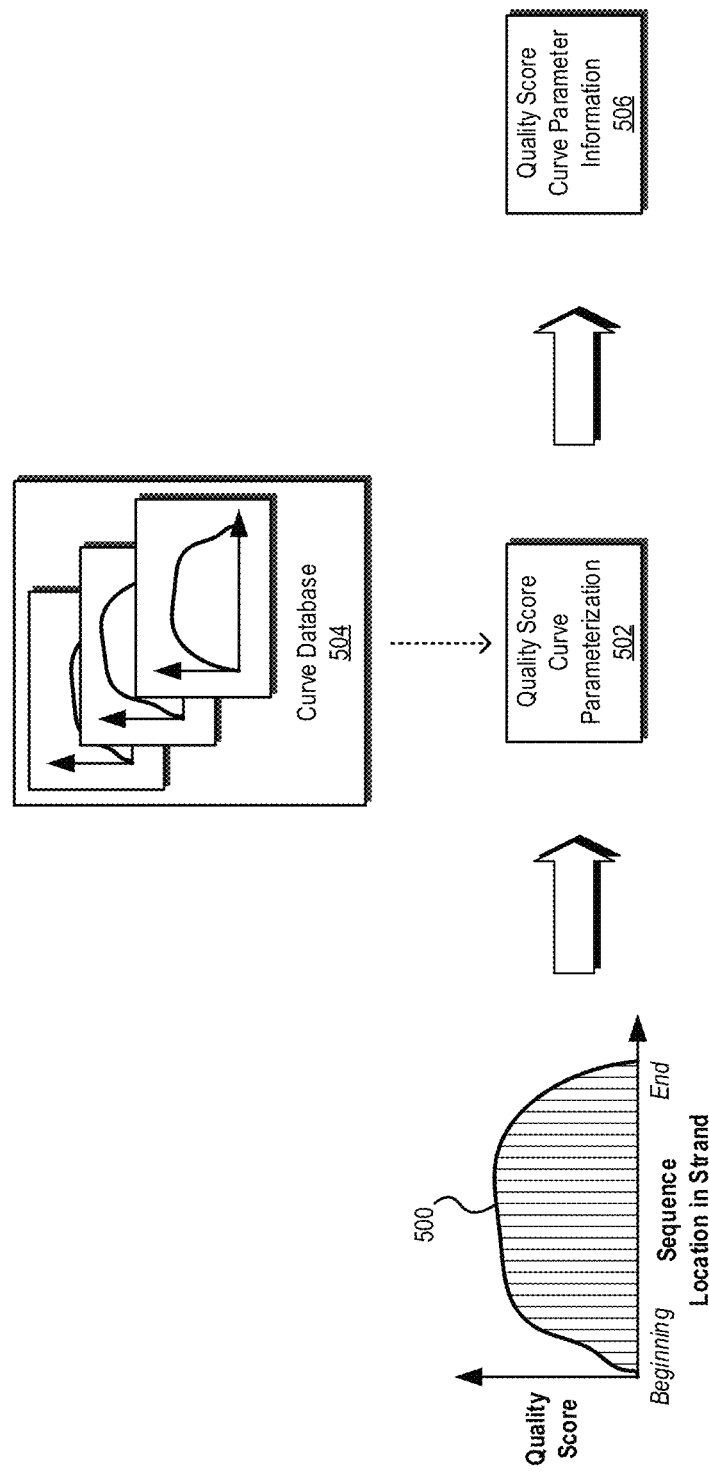
FIG. 5 illustrates an example of the generation of quality score curve parameter information consistent with embodiments of the present disclosure.

FIG. 5 illustrates an example of the generation of quality score curve parameter information 506 consistent with embodiments of the present disclosure. In certain embodiments, sequence data may be associated with one or more quality scores that may represent a relative confidence in a particular read of a location in a particular sequenced strand. That is, the quality score may measure a quality and/or relative likelihood that the identification of the nucleobases generated by the sequencing system at a particular location is accurate. Discrete quality score data may be represented by an associated quality score curve 500.

Quality scores may be influenced based, at least in part, on a position of a sequence location relative to an associated sequenced strand. For example, as reflected in the illustrated quality score curve 500, quality scores may be generally lower for sequence locations at the ends of a sequence strand of DNA than in the middle of a sequence strand (e.g., due to systematic errors introduced by the handling of the partial strand ends during the sequencing process and/or the like).

Consistent with embodiments disclosed herein, a quality score curve 500 may be analyzed to determine one or more parameters that describe the quality score curve 500. For example, as illustrated, a quality score curve parameterization module 502 executing on an associated system may receive a quality score curve 500 and/or associated discrete quality score data, analyze the received curve and/or data, and generate corresponding quality score curve parameter information 506. In certain embodiments, the quality score curve parameter information 506 associated with the analyzed quality score curve 500 and/or associated quality score data may be communicated and/or stored rather than discrete quality score data and/or the entire associated quality curve, thereby realizing certain storage and/or communication efficiencies.

Quality score curve parameter information 506 may be generated based on quality score curve 500 and/or associated discrete quality score data using a variety of methods. For example, in some embodiments, a quality score curve 500 may be analyzed using polynomial curve fitting methods, and variables, coefficients and/or parameters associated with a fitted polynomial describing an approximation of the quality score curve 500 may be reflected in quality score curve parameter information 506. Using the quality score curve parameter information 506, the quality score curve 500 may be reconstructed.

In other embodiments, other curve fitting methods may be used in connection with generating quality score parameter information 506. For example, in certain embodiments, sinusoid and/or other trigonometric function curve fitting methods may be employed to generate quality score parameter information 506 including variables, coefficients, and/or parameters reflective of the quality score curve 500. Similarly, geometric curve fitting methods may also be employed to generate quality score parameter information 506.

In yet further embodiments, a quality score curve 500 may be compared against one or more reference curves included in a reference curve database 504. One or more adjustments to the reference curve(s) may be identified that describe the quality score curve 500 relative to the reference curve(s). By applying the one or more adjustments to an associated reference curve(s), the quality score 500 and/or an approximation thereof may be generated and/or otherwise reconstructed.

In certain embodiments, reference curves included the reference curve database 504 may be categorized based on an associated shape. A quality score curve 500 may be analyzed against curves included in the reference curve database 504 and/or associated categories of curve until a reference curve and/or category can be identified that has a shape that approximates within a threshold degree a shape of the quality score curve 500. One or more one or more variables, coefficients, and/or parameters may be generated that, when applied to the identified reference curve and/or associated category, result in an adjusted reference curve that approximates the quality score curve 500. An indication of the reference curve and/or an associated category and the generated variables, coefficients, and/or parameters may be stored and/or communicated instead of the discrete quality score data and/or the entire associated quality score curve 500, thereby realizing certain storage and/or communication efficiencies.

In further embodiments, the reference curve database 504 may include a plurality of reference curves and a plurality of predefined adjustments to the reference curves. A quality score curve 500 may be analyzed and/or otherwise compared to reference curves included in the reference curve database 504 and/or reference curves included in the reference curve database 504 adjusted according to one or more of the predefined adjustments to identify a reference curve and/or an associated predefined adjustment that approximates the quality score curve 500 within a certain threshold and/or degree. An indication of the reference curve and/or an associated predefined adjustment may be stored and/or communicated as a representation of the discrete quality score data and/or quality score curve 500.

In certain embodiments, the reference curves and/or other information included in the reference curve database 504 and/or associated reference curve categories may be generated in a variety of ways. In some embodiments, reference curves may be categorized according to a degree of a polynomial required to describe the curve. In further embodiments, a neural network may be trained to recognize the shapes of curves a number of example reference curves (e.g., examples of a large number of quality score curves associated with actual sequence read data), determine the similarity between example curves, and categorize and/or otherwise sort them accordingly.

In embodiments where reference curves are categorized based on associated polynomial representations, a distortion function used to represent a difference between a quality score 500 curve and an associated reference may be generated by determining a difference between the coefficients of a polynomial associated with the reference curve and a fitted polynomial for the quality score curve 500. In embodiments where referenced curves are categorized based on recognized curve shapes (e.g., as may be determined by a neural network), a distortion matrix may be generated that offsets, shears, and/or scales the reference curve to arrive at a curve that approximates the quality score curve 500. If a quality score curve 500 is relatively similar to a reference curve with the exception of a few extreme values, the reference curve may be used to represent the quality score curve adjusted according to the extreme values.

In certain embodiments, a plurality of curve fitting methods may be used to generate quality score curve parameter information 506 associated with a quality score curve 500 and/or different portions thereof. For example, a first curve fitting method (e.g., polynomial approximation) may be used to generate parameter information associated with a beginning portion of a quality score curve 500, a comparison with reference curves included in a reference curve database 504 may be used to generate parameter information associated with a middle portion of a quality score curve 500, and a sinusoid and/or other trigonometric function curve fitting method may be used to generate parameter information associated with an end portion of a quality score curve 500.

In further embodiments, different curve fitting methods may be used to generate quality score parameter information 506 associated with different quality score curves. In some embodiments, a size and/or complexity of resulting quality score parameter information 506 may influence which curve fitting method is selected to generate quality score parameter information 506 associated with a particular quality score curve. For example, a first quality score curve may be approximated by a relatively low order polynomial or a relatively complex distortion matrix associated with a reference curve, whereas a second quality score curve may be approximated by a relatively high order polynomial and a relatively simple distortion matrix associated with a reference curve. Accordingly, the first quality score curve may be approximated using polynomial approximation and the second quality score curve may be approximated using a reference curve and an associated distortion matrix. In this manner, efficiencies in the storage and/or transmission of the first and second quality score curves may be realized.

Although certain embodiments are discussed in connection with storing and/or transmitting quality score curve data using various curve approximation methods, it will be appreciated that the disclosed embodiments may be further used in connection with efficiently storing and/or communicating any suitable type of similar information.

Figure 6:
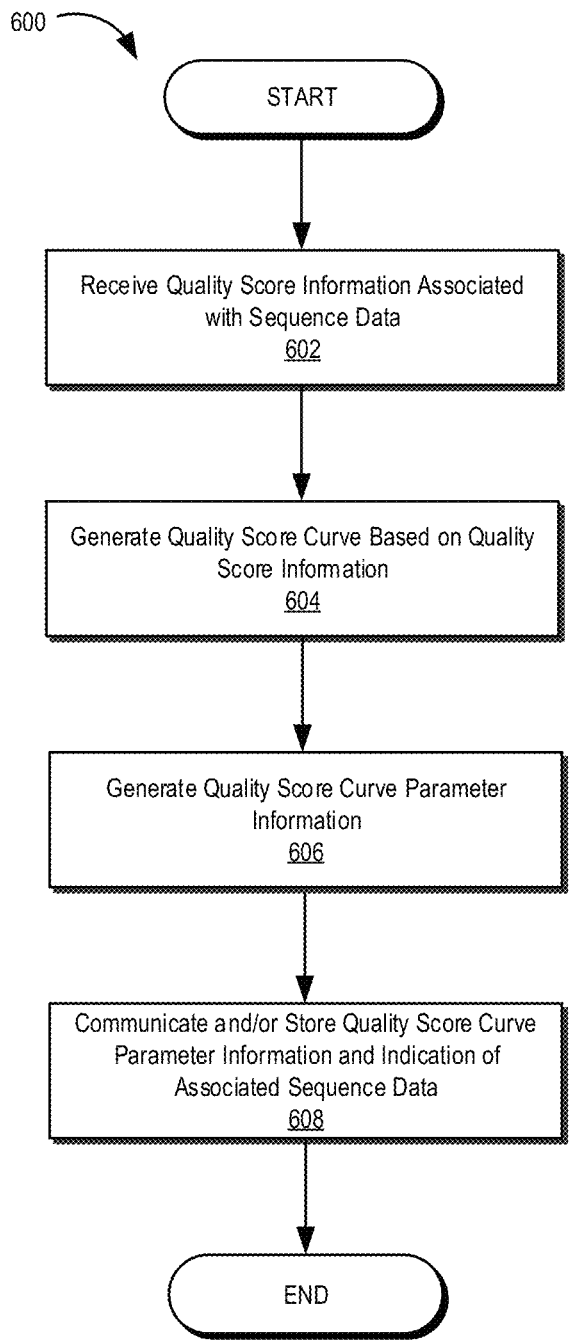
FIG. 6 illustrates a flow chart of an example of a method for storing and/or communicating quality score information consistent with embodiments of the present disclosure.

FIG. 6 illustrates a flow chart of an example of a method 600 for storing and/or communicating quality score information consistent with embodiments of the present disclosure. The illustrated method 600 may be implemented in a variety of ways, including using software, firmware, hardware, and/or any combination thereof. In certain embodiments, various aspects of the method 600 and/or its constituent steps may be performed by a genomic data storage and/or processing system and/or any other suitable system or combination of systems. In some embodiments, the illustrated method 600 may facilitate the generation and/or communication of quality score information using quality score curve parameterization methods.

At 602, quality score information associated with sequence data may be received. In some embodiments, the quality score information may be associated with unaligned sequence read data and may represent a relative confidence in a particular read at a particular location. The quality score information may comprise a plurality of discrete quality scores, each score being associated with a location of the read locations associated with the sequence data.

Based on the quality score information, an associated quality score curve may be generated at 604. In some embodiments, the quality score curve may comprise a curve fitted to a plurality of discrete quality scores associated with read locations in unaligned sequence read data associated with a partial strand of genetic material.

At 606, quality score curve parameter information may be generated based on the quality score curve generated at 604. The quality score curve parameter information may be used to approximate the quality score curve. A variety of methods may be used to generate the quality score parameter information including, for example, polynomial, sinusoidal, trigonometric, geometric, and/or other curve fitting methods, comparing a quality score with one or more reference curves, and/or other suitable approximation methods. At 608, the quality score curve parameter information and, if applicable, and indication of an associated reference curve and/or the associated sequence data may be stored and/or communicated (e.g., transmitted to different system) at 608. In certain embodiments, communicating and/or storing the quality score curve parameter information instead of discrete quality score data and/or the entire associated quality curve may be associated certain storage and/or communication efficiencies.

In certain embodiments, the quality score information and/or associated quality score curve may be reconstructed using the generated quality score curve parameter information. For example, the quality score curve parameter information may comprise various coefficients associated with a polynomial approximation of the quality score curve and, based on the polynomial approximation, the original quality score information may be approximated. In other embodiments, the quality score curve parameter information may comprise various differences between the quality score curve and one or more reference curves, and the quality score curve may be approximated and/or otherwise reconstructed by applying the differences to the one or more reference curves.

Figure 7:
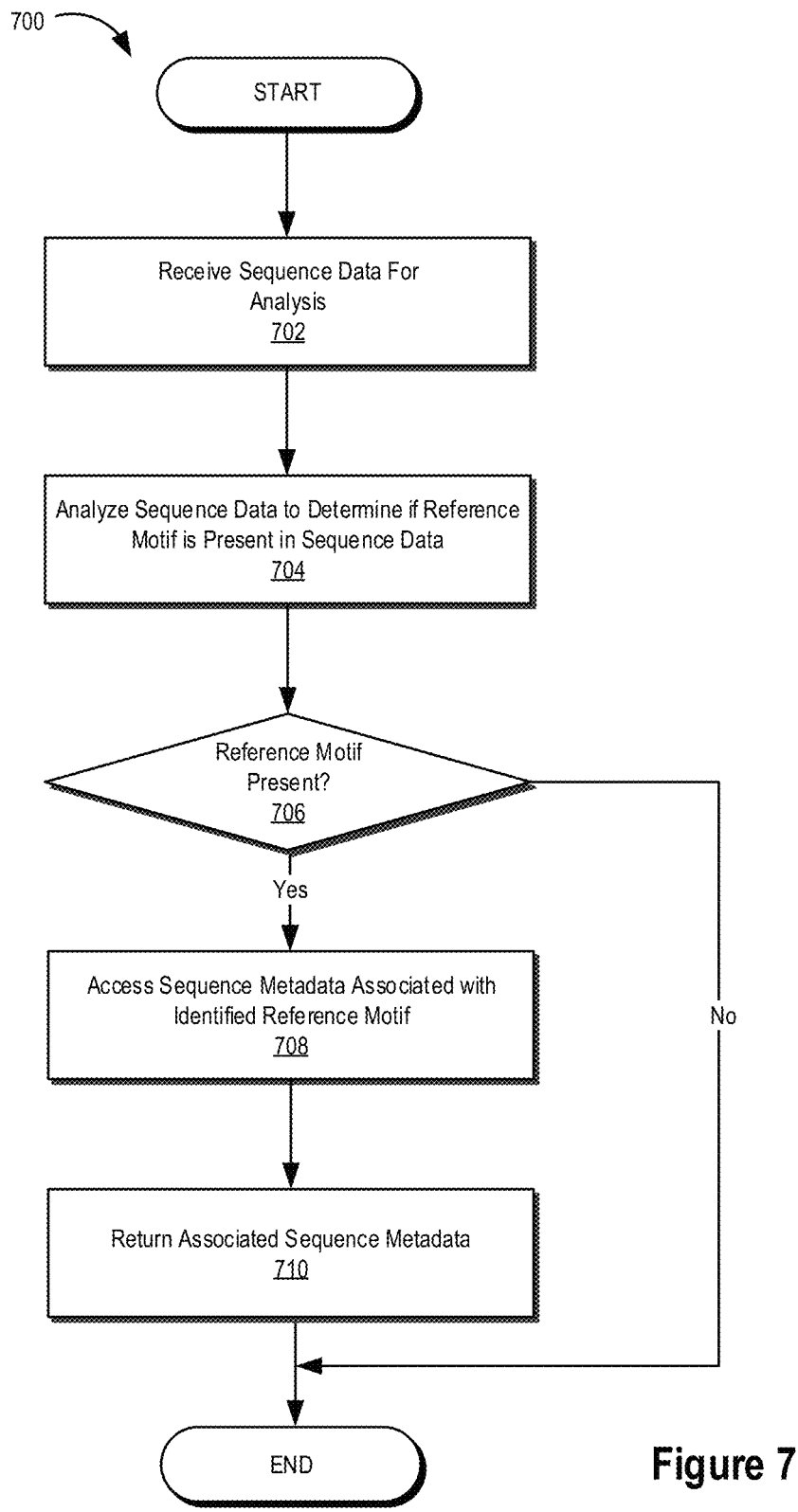
FIG. 7 illustrates a flow chart of a method for analyzing sequence read data consistent with embodiments of the present disclosure.

FIG. 7 illustrates a flow chart of a method 700 for analyzing sequence read data consistent with embodiments of the present disclosure. The illustrated method 700 may be implemented in a variety of ways, including using software, firmware, hardware, and/or any combination thereof. In certain embodiments, various aspects of the method 700 and/or its constituent steps may be performed by a genomic data storage and/or processing system and/or any other suitable system or combination of systems.

In some embodiments, the illustrated method 700 may facilitate relatively efficient analysis of sequence read data using reference motifs. For example, if there is an interest in calling and/or otherwise analyzing a relatively simple characteristic of an organism associated with sequence read data, reference motifs associated with metadata and/or other information may be used to speed the identification and/or analysis of such characteristics. In certain embodiments, this may be particularly useful for example, in connection with quickly identifying infectious microbes (e.g., in a hospital setting and/or the like), identifying an organism's species and/or classification, and/or identifying other characteristics and/or traits that may be have an association with a reference motif.

At 702, sequence data and/or an associated request may be received by a genomic data storage and/or processing system for analysis and/or processing. The sequence data may be analyzed at 704 to determine if the sequence data includes one or more reference motifs. As discussed above, the reference motifs may comprise one or more sequence patterns and may be included in a table that comprises a plurality of reference motifs and associated reference sequences.

In certain embodiments, the reference motifs may be associated with metadata and/or other information that may be included in the reference motif and/or reference sequence table. The metadata and/or other information may, among other things, delineate information relating to characteristics, traits, and/or classification of an organism associated with sequence read data that includes the reference motif. For example, metadata and/or other information may identify a likelihood that an organism has particular characteristics if associated sequence data includes certain reference motifs. Non-limiting examples of metadata and/or other information associated with reference motifs is presented below in Table 1.

TABLE 1

| Reference Motif | Associated Metadata |
|---|---|
| Reference Motif 1 | 100% Likelihood Metazoa |
| Reference Motif 2 | 99.9% Likelihood Bilatera |
| Reference Motif 3 | 99% Likelihood Mammalia |
| Reference Motif 4 | 90% Likelihood Hominidae |

TABLE 1-continued

| Reference Motif | Associated Metadata |
| --- | --- |
| Reference Motif 5 | Associated with 20 Human Characteristics |
| Reference Motif 6 | Sequences Found in Less Than 10% of Humans |

If it is determined at 706 that the sequence data does not include a reference motif included in the reference motif table, the method 700 may end. If, however, it is determined at 706 that the sequence data includes a reference motif included in the reference motif table, the method 700 may proceed to 708, where metadata and/or other information associated with the identified reference motif may be accessed. In response to the request received at 702, the metadata and/or other information accessed at 708 may be returned at 710.

In certain embodiments, by identifying a reference motif within unaligned sequence read data that is associated with corresponding metadata and/or other information, relatively efficient sequence calls and/or analysis may be achieved without needing to align the unaligned sequence read data. For example, if unaligned sequence read data includes reference motifs 1-5 of Table 1, it may be determined that there is a high likelihood an organism associated with the unaligned sequence read data is a human without necessarily having to perform a computationally intensive alignment process.

Figure 8:
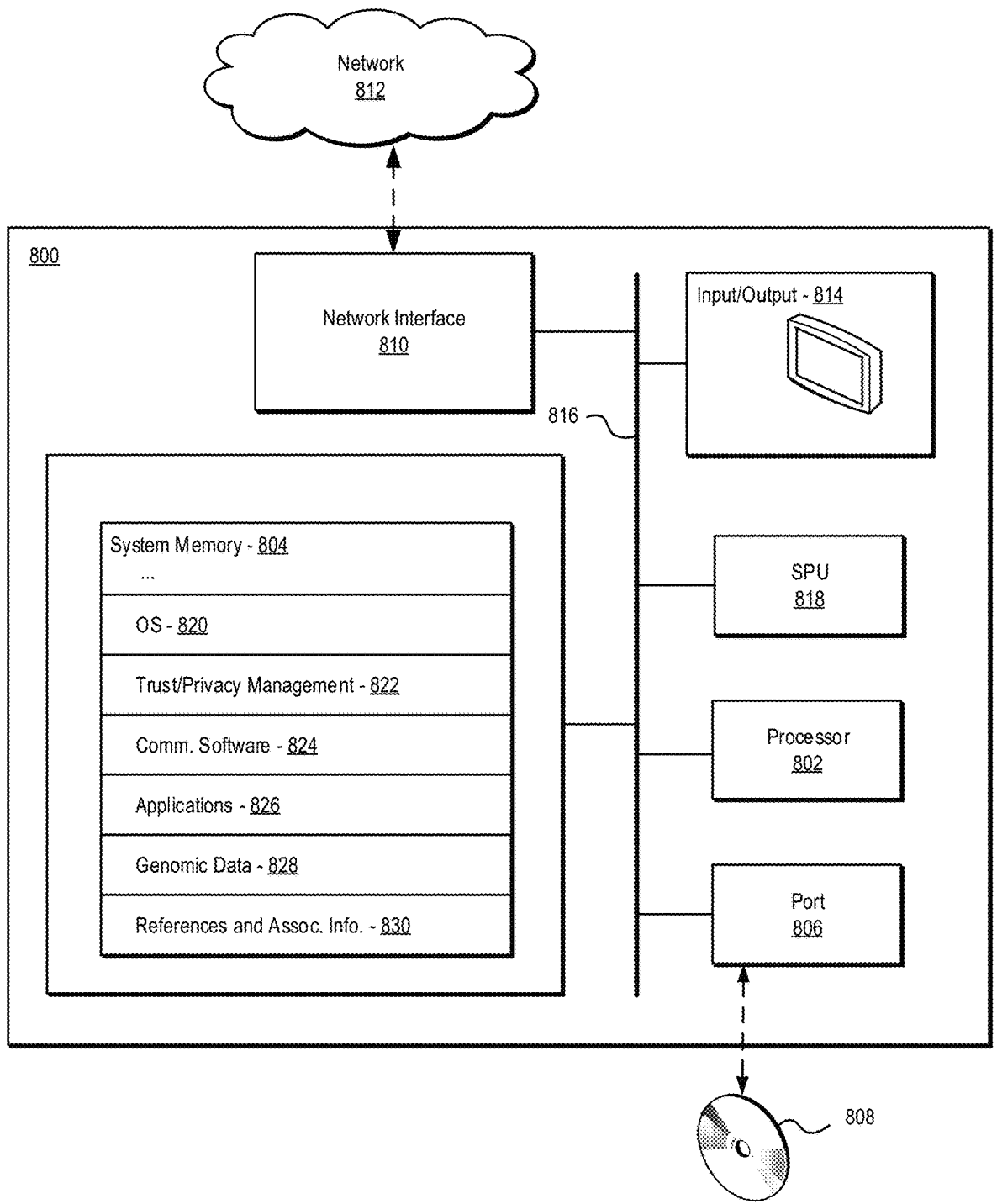
FIG. 8 illustrates an example of a system that may be used to implement certain embodiments of the systems and methods of the present disclosure.

FIG. 8 illustrates an example of a system 800 that may be used to implement certain embodiments of the systems and methods of the present disclosure. Certain elements associated with the illustrated exemplary system 800 may be included in one or more systems configured to store, communicate, and/or otherwise use genomic data, and/or any other system configured to implement embodiments of the disclosed systems and methods. As illustrated in FIG. 8, the system 800 may include: a processing unit 802; system memory 804, which may include high speed random access memory ("RAM"), non-volatile memory ("ROM"), and/or one or more bulk non-volatile non-transitory computer-readable storage mediums (e.g., a hard disk, flash memory, etc.) for storing programs and other data for use and execution by the processing unit 802; a port 806 for interfacing with removable memory 808 that may include one or more diskettes, optical storage mediums, and/or other non-transitory computer-readable storage mediums (e.g., flash memory, thumb drives, USB dongles, compact discs, DVDs, etc.); a network interface 810 for communicating with other systems via one or more network connections 812 using one or more communication technologies; a user interface 814 that may include a display and/or one or more input/output devices such as, for example, a touchscreen, a keyboard, a mouse, a track pad, and the like; and one or more busses 816 for communicatively coupling the elements of the system 800.

In some embodiments, the system 800 may, alternatively or in addition, include an SPU 818 that is protected from tampering by a user of the system 800 or other entities by utilizing secure physical and/or virtual security techniques. An SPU 818 can help enhance the security of sensitive operations such as personal information management, trusted credential and/or key management, privacy and policy management, versioning control and/or management, and other aspects of the systems and methods disclosed herein. In certain embodiments, the SPU 818 may operate in a logically secure processing domain and be configured to protect and operate on secret and/or otherwise secure information. In some embodiments, the SPU 810 may include internal memory storing executable instructions or programs configured to enable the SPU to perform secure operations.

The operation of the system 800 may be generally controlled by the processing unit 802 and/or the SPU 818 operating by executing software instructions and programs stored in the system memory 804 (and/or other computer-readable media, such as removable memory). The system memory 804 may store a variety of executable programs or modules for controlling the operation of the system 800. For example, the system memory may include an operating system ("OS") 820 that may manage and coordinate, at least in part, system hardware resources and provide for common services for execution of various applications and a trust and privacy management system 822 for implementing trust and privacy management functionality including protection and/or management of secure data through management and/or enforcement of associated policies. The system memory 804 may further include, without limitation, communication software 824 configured to enable in part communication with and by the system 800; one or more applications 826; genomic data 828 which may include unaligned sequence read data; reference motifs, reference sequences, and/or associated metadata and/or other information 830; and/or any other information, modules, and/or applications configured to implement embodiments of the systems and methods disclosed herein.

The systems and methods disclosed herein are not inherently related to any particular computer, device, service, or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers, at one site or distributed across multiple sites and interconnected by a communication network.

Software embodiments may be implemented as a computer program product that comprises a non-transitory storage medium configured to store computer programs and instructions, that when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, an optical storage medium, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein but may be modified within the scope and equivalents of the appended claims.

What is claimed is:

1. A method for efficiently communicating genomic information, comprising:

providing, by a second computing system to a first computing system, a request to transfer unaligned genomic sequence read data and associated quality score information to the second computing system;

receiving, from the first computer system, a response to the request comprising a variant list, one or more indications of first and second reference motifs, and quality score curve parameter information:

the variant list indicating differences between at least a first portion of the unaligned genomic sequence read data and at least a portion of a first reference sequence and differences between at least a second portion of the unaligned genomic sequence read data and at least a portion of a second reference sequence, the variant list being generated based on a comparison between the first portion of the unaligned genomic sequence read data and the at least a portion of the first reference sequence, and a comparison between the second portion of the unaligned genomic sequence read data and the at least a portion of the second reference sequence:

the second reference sequence being selected from a reference table, the second reference sequence being associated with a second reference motif, the second reference motif identified as being included in the unaligned genomic sequence read data and being different than a first reference motif;

the first reference sequence being selected from the reference table, the first reference sequence being associated with the first reference motif, the first reference motif identified as being included in the unaligned genomic sequence read data; and the reference table comprising a plurality of reference motifs and a plurality of reference sequences, wherein each reference motif of the plurality of reference motifs is associated with a reference sequence of the plurality of reference sequences; and the quality score curve parameter information being generated based on a quality score curve, the quality score curve parameter information characterizing the quality score curve:

the quality score curve being generated based on the quality score information, the quality score information being associated with the unaligned genomic sequence read data;

reconstructing, by the second computing system, the unaligned genomic sequence read data based on the variant list and the one or more indications of first and second reference motifs without transferring the unaligned genomic sequence read data to the second computing system; and reconstructing, by the second computing system, at least an approximation of the quality score curve based on the quality score curve parameter information without transferring the quality score information associated with the unaligned genomic sequence read data to the second computing system.

2. The method of claim 1, wherein the reference table comprises a locally-stored reference table managed by the first computing system, the locally-stored reference table accessed to identify the first and second reference motifs.

3. The method of claim 1, wherein the reference table comprises a remotely-stored reference table, the remotely-stored reference table accessed from a third-party service to identify the first and second reference motifs.

4. The method of claim 1, wherein the indication of the first and second reference motifs comprises a first pointer to the at least a portion of the first reference sequence and a second pointer to the at least a portion of the second reference sequence.

5. The method of claim 1, wherein the quality score curve parameter information comprises-polynomial coefficients associated with a polynomial approximation of the quality score curve.

6. The method of claim 1, wherein the quality score parameter information comprises-parameters associated with a trigonometric approximation of the quality score curve.

7. The method of claim 6, wherein the trigonometric approximation comprises a sinusoidal approximation.

8. The method of claim 1, wherein the quality score parameter information comprises indications of differences between the quality score curve and at least one of one or more reference quality score curves.

9. The method of claim 8, wherein the indications of differences between the quality score curve and at least one of the one or more reference quality score curves comprise at least one predefined difference.

10. The method of claim 1, further comprising receiving the quality score curve by the second computer system.

* * * * *